US00PP24062P2

(12) United States Plant Patent
Falstad

(10) Patent No.: US PP24,062 P2
(45) Date of Patent: Dec. 3, 2013

(54) ***HIBISCUS* PLANT NAMED 'BERRYLICIOUS'**

(50) Latin Name: ***Hibiscus* hybrid (L.)**
Varietal Denomination: Berrylicious

(75) Inventor: Clarence H. Falstad, Holland, MI (US)

(73) Assignee: Walters Gardens Inc, Zeeland, MI (US)

( * ) Notice: Subject to any disclaimer, the term of this patent is extended or adjusted under 35 U.S.C. 154(b) by 127 days.

(21) Appl. No.: 13/385,988

(22) Filed: Mar. 19, 2012

(51) Int. Cl.
*A01H 5/00* (2006.01)

(52) U.S. Cl.
USPC ..... Plt./257

(58) Field of Classification Search
USPC ..... Plt./257
See application file for complete search history.

(56) References Cited

U.S. PATENT DOCUMENTS

| | | | | |
|---|---|---|---|---|
| PP11,853 | P2 * | 5/2001 | Fleming et al. | Plt./257 |
| PP11,854 | P2 * | 5/2001 | Fleming et al. | Plt./257 |
| PP18,938 | P2 * | 6/2008 | Smith | Plt./257 |

OTHER PUBLICATIONS

UPOV PLUTO 201303 Database CA Citation for 'Berrylicious' Jul. 29, 2011.*

* cited by examiner

*Primary Examiner* — Wendy C Haas

(57) ABSTRACT

A new and distinct cultivar of hardy herbaceous *Hibiscus* hybrid plant named 'Berrylicious' comprising a winter-hardy perennial, naturally-compact, heavily branched stems, medium green leaves producing numerous mauve-lavender flowers with dark-raspberry eyes on nearly flat flowers over at least 12 weeks during the summer until frost. The new plant, *Hibiscus* 'Berrylicious' shows resistance to black spot fungus and resists deer browsing and the ruffled flowers resist wind and sun.

1 Drawing Sheet

Botanical classification: *Hibiscus* hybrid (L.).
Variety denomination: 'Berrylicious'.

BACKGROUND AND ORIGIN OF THE PLANT

The present invention relates to the new and distinct hardy, herbaceous, *Hibiscus* plant, *Hibiscus* 'Berrylicious' hybridized by Clarence H. Falstad in the summer of 2007 at a nursery in Zeeland, Mich. The new plant, originally labeled # 07-115-X, is from a cross between the proprietary hybrid # 05-21-01 (not patented) (female pod parent) times the proprietary hybrid # 04-18-06 (not patented) (male pollen parent). Both parents have a complex mixture of species in them, most likely including the species: moscheutos, coccineus and laevis. *Hibiscus* 'Berrylicious' has been propagated both by stem cuttings and tissue culture at the same nursery in Zeeland, Mich. The resultant plants have been found to be stable and true to type in successive generations of asexual reproduction.

BRIEF SUMMARY OF THE PLANT

*Hibiscus* 'Berrylicious' differs from its parents as well as all other *Hibiscus* known to the applicant in many traits. The foliage color of 'Berrylicious' is medium to light green with rare light burgundy tinting at the margin. The foliage shape of 'Berrylicious' is heterophyllous, depending on the time of year and position on the stem. Most leaves are dissected, mostly tri-lobed, rarely five-lobed with some either young leaves or those on immature plants being ovate. The flowers of 'Berrylicious' are nearly flat-faced with mauve lavender petals and deep-strawberry eyes. The most similar *Hibiscus* to 'Berrylicious' are *Hibiscus* 'Fantasia' U.S. Plant Pat. No. 11,853 and *Hibiscus* 'Plum Crazy' U.S. Plant Pat. No. 11,854.

The new plant has greater branching habit than either 'Fantasia' or 'Plum Crazy'. The flowers of 'Berrylicious' are larger, lighter lavender colored than 'Plum Crazy', and the foliage is lighter green with less burgundy tinting and more dissected than 'Plum Crazy'. The flowers of 'Fantasia' are smaller, more reddish and more cupped than the new plant, and the pollen on the new plant is a clear, bright, yellow rather than the dirty, more gray-yellow of 'Fantasia'. Foliage of the new plant is lighter green and more dissected than 'Fantasia'.

In comparison to the parents, both #05-21-01 and #04-18-06 have reddish flowers. The new plant is also intermediate in plant height and flower size.

*Hibiscus* 'Berrylicious' is a unique hardy herbaceous hibiscus with the following combined traits:

1. Winter-hardy, upright rounded habit with good branching.
2. Many nearly flat-faced flowers with mauve lavender petals, shiny deep-strawberry eyes and contrasting, bright, clear-yellow pollen.
3. Dissected foliage of medium to light green with reddish veins.

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, source and direction may cause the appearance of minor variation in color. The plant in the drawing is a two year-old plant grown in the full sun field in Ottawa County, Mich. with water and fertilizer applied as needed but no growth regulators.

FIG. 1 shows the plant in mid-season flowering with flowers, buds and dissected foliage;

DETAILED BOTANICAL DESCRIPTION

The following descriptions and color references are based on the 2001 edition of The Royal Horticultural Society Colour Chart except where common dictionary terms are used. The new plant, *Hibiscus* 'Berrylicious', has not been observed under all possible environments. The phenotype may vary slightly with different environmental conditions, such as temperature, light, fertility, moisture and maturity levels, but without any change in the genotype. The following observations and size descriptions are of two-year old plants in the loamy-sand unshaded field trials of a nursery in Zeeland, Mich. and production field rows in Allegan County, Mich., respectively, both with supplemental fertilizer and water as needed. The plants are natural habit and were not treated with plant growth regulators, nor were they pinched at any time in the growth year.

Parentage: Proprietary hybrid # 05-21-01 (not patented) (female or pod parent) times the proprietary hybrid # 04-18-06 (not patented) (male or pollen parent).

Propagation:

*Method*.—Stem tip cuttings and sterile plant tissue culture division. Time to initiate roots from tissue culture: about two weeks.

*Rooting habit*.—Normal, branching, thick, developing to about 4 cm diameter, fleshy; root color creamy white between RHS 159A and lighter than RHS 159 D depending on soil type.

*Crop time*.—Under normal summer growing conditions 10 to 14 weeks to flower in a field row from a 2.5 cm diameter plug. Plant vigor is very good.

Plant description:

*Plant shape and habit*.—Hardy herbaceous perennial with about three to four stems on one-season old plants and 10 to 20 stems on two-season old plants; stems thick upright, nearly 80 degrees from horizontal, upright and heavily branched main stems producing a rounded mound on two-year old plants; about 12 primary branches per main stem protruding at 45° to 55° angle from the vertical main stem, secondary branches on the lower one third of the primary branches; main stems size about 80.0 cm to 85.0 cm tall and 2.2 cm diameter at base on two year-old plants; primary branch size about 50.0 cm long and 1.2 cm diameter; secondary branches about 12.0 cm long and 3.0 mm diameter (shorter at the upper nodes); stem and branch color between RHS 139C and RHS 144A with limited tinting of nearest RHS 185B.

*Plant size*.—Unpinched plant with stems up to 85 cm tall from soil line, and diameter at base average about 2.2 cm; overall plant about 95 cm wide at the widest point.

*Internode length*.—Of unpinched plant between 3.5 to 7.0 cm, longest in mid-stem; average about 5.0 cm.

*Foliage description*.—Alternate; dentate; glabrous; heterophyllous; ovate equilateral base and acute apex; tri-lobed with base lobes cleft 45 to 90 degrees; shape hastate to palmatifid with some lower leaves oblong ovate with two lobes about 1.5 cm long; texture dull above and below; palmately veined; leaf size 10.0 to 13.0 cm long and 10.0 to 13.0 cm wide with average 11 cm long and 11.0 cm wide, becoming smaller in distal portion of stem.

*Foliage color*.—Adaxial side between RHS 137B and RHS 138A with occasional light burgundy tinting mostly at leaf margins of young leaves of between RHS N186C and RHS N186D; abaxial side between RHS 139C and RHS 139D with rare tinting of nearest RHS 187B.

*Veins*.—Palmate; slightly recessed above and slightly raised below.

*Vein color*.—Primary and secondary adaxial veins between RHS 138 B and RHS 138C developing slightly reddish tint between RHS 185B and RHS 185C toward center; abaxial veins between RHS 144D and RHS 143D, secondary veins the same color as surrounding leaf tissue on abaxial side.

*Petioles*.—Average size 3.0 cm long and 3.0 mm wide; mostly cylindrical with proximal petioles slightly plano-convex; color above nearest RHS 182B, green below between RHS 144C and RHS 147C with greyed purple overtones nearest RHS 183C.

Flower description:

*Buds*.—One day prior to opening about 7.5 cm long and 4.0 cm in diameter, acute apex and bluntly rounded base, unopened petals wrinkled at veins, exposed petal color between RHS 77B and RHS 77A; just after first showing petals, buds are about 2.4 cm long and 3.0 cm in diameter; ovoid with acute rounded apex, carinate at the fusion seam of the sepals; sepal color between RHS 144B and RHS 144A with veining and sepal carina same as surrounding tissue.

*Epicalyx*.—Entire, smooth, glabrous, linear with sharply acute apex, curved around sepals; 11 to 12 per flower; 2.5 cm long tapering to base of 2.5 mm wide; adaxial color RHS 144A, abaxial color RHS 144B.

*Sepals*.—5, proximal half connate forming campanulate star-shaped calyx; acute apex; margin entire, edentate; about 4.5 cm long and 5.5 cm wide; abaxial color between RHS 144A and RHS 143B; adaxial color between RHS 144A and RHS 144B; five primary sepal veins nearest RHS 144D on inside and outside.

*Flowers*.—Solitary, 12 to 18 per main stem without pinching; petals opening to about 180 degrees flat; upward and outwardly facing; average 20.0 cm across, larger in early part of flowering season; persist for one to two days; effective for at least 12 weeks beginning mid July and lasting into October; no detectable fragrance.

*Petals*.—Five; glabrous, slightly lustrous, adnate to the androecium, imbricate to about 110% overlapping at widest part (petals completely overlapping the next petal and 10% of the petal in the position two over); shape: rounded; margins: entire, edentate; apex: rounded; base: short claw-like; average 11.0 cm long and 16.0 cm wide at widest portion (larger in earlier part of flowering season); dark-strawberry eye about 5.0 cm diameter; petal veins ribbed in back from apex nearly to base and gathered 3.0 to 4.0 mm between veins on front producing a ruffled effect.

*Petal color*.—Front between RHS N74C and RHS 72C, eye of between RHS 46A and RHS 53A; back color between RHS N57D and RHS 64C, eye nearest RHS 67A; petal veins starts about RHS 46A in center continuing eye color and gradually becomes the same color as surrounding petal on front and on back nearest RHS 72C.

*Gynoecium*.—Style enclosed in column that is average 5.8 cm long and 1.5 cm wide at base; column color nearest RHS N155D at base with tinting at apical end of nearest RHS 46A; Style: protrudes above column about 2.0 cm and is split into five branches in the last 10.0 mm with diameter 2.0 mm; style branches color nearest RHS N57B; Stigma: five; globose, puberulose, about 3.0 mm in diameter, nearest RHS 57C; Ovary: apex acute, 1.0 cm diameter and 1.0 cm tall above calyx base; color: closest to RHS 150D.

*Androecium*.—Filaments: numerous, about 140; less than 1.0 mm in diameter and about 5.0 mm long; attached to nearly the entire length of column; nearest RHS N66C; Anthers: reniform; about 2.0 mm long and 1.0 mm wide; nearest RHS 11B; Pollen: numerous, globose, less than 0.1 mm long, nearest RHS 12C.

*Pedicel*.—From base of sepal to abscission point average 1.5 cm long and 4.0 mm wide on early flowers decreasing in distal flowers; color nearest RHS 144A with high light exposure.

*Peduncle*.—Flowers are easily visible held out average 5.5 cm long from abscission point to stem and 4.0 mm wide on early flowers shortening to about 3.0 cm higher on stem; color nearest RHS 144A and tinting of nearest RHS 186B with light exposure.

Fruit: Few, loculicidal capsule; glabrous; globose, occasionally with abruptly acute apex; RHS N199B when mature.

*Seed*.—Minutely floccose, globose to slightly reniform; 3.0 to 4.0 mm in diameter; RHS 200A.

Disease resistance: Showed some resistance to foliar black spot fungus compared to other hibiscus in the general facility, and be generally free of deer browsing. Other resistance beyond that of other hardy hibiscus cultivars has not been observed. The plant grows best with plenty of moisture and adequate drainage, but is able to tolerate some drought when mature. The flowers are able to withstand significantly more wind and sun than the typical flat petals of other hibiscus. Hardiness at least from USDA zone 4 through 9.

I claim:

1. A new cultivar of hardy herbaceous *Hibiscus* hybrid plant named 'Berrylicious' as herein illustrated and described, comprising a winter-hardy perennial, naturally-compact, heavily branched stems, medium green leaves producing numerous mauve-lavender flowers with dark-raspberry eyes on nearly flat flowers over at least 12 weeks during the summer until frost suitable for potted plant culture, landscaping as specimen or en masse.

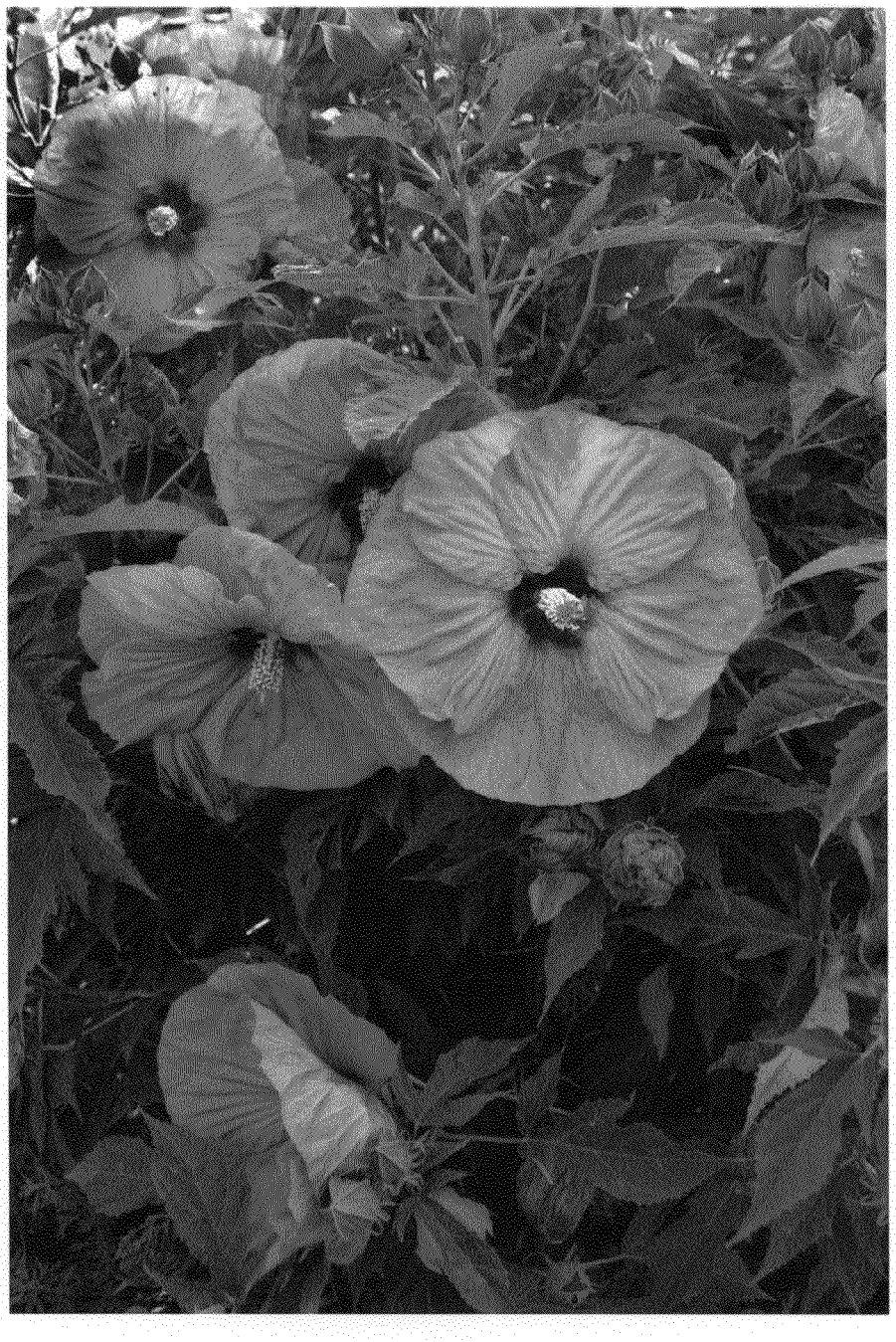

* * * * *